United States Patent [19]

Gordon et al.

[11] Patent Number: 5,058,856
[45] Date of Patent: Oct. 22, 1991

[54] THERMALLY-ACTUATED MICROMINIATURE VALVE

[75] Inventors: Gary B. Gordon, Saratoga; Phillip W. Barth, Palo Alto, both of Calif.

[73] Assignee: Hewlett-Packard Company, Palo Alto, Calif.

[21] Appl. No.: 697,149

[22] Filed: May 8, 1991

[51] Int. Cl.$^5$ .............................................. F16K 31/70
[52] U.S. Cl. ........................................ 251/11; 357/26
[58] Field of Search ...................... 251/11; 357/26, 28

[56] References Cited

U.S. PATENT DOCUMENTS

| | | | |
|---|---|---|---|
| 4,248,402 | 2/1981 | Meckstroth | 251/11 |
| 4,474,889 | 10/1984 | Terry et al. | 436/161 |
| 4,581,624 | 4/1986 | O'Connor | 357/26 |
| 4,869,282 | 9/1989 | Sittler et al. | 137/15 |
| 4,943,032 | 7/1990 | Zdeblick | 251/11 |

OTHER PUBLICATIONS

"Silicon Micromechanical Devices," James B. Angell et al., *Scientific American*, Apr. 1983, pp. 44–55.
"Electrically-Activated, Micromachined Diaphragm Valves," Hal Jerman, *Technical Digest IEEE, Sensor and Actuator Workshop*, Jun. 1990, pp. 65–69.

*Primary Examiner*—Robert G. Nilson

[57] ABSTRACT

A microminiature valve having radially spaced, layered spider legs, with each leg having first and second layers of materials having substantially different coefficients of thermal expansion. The legs include heating elements and are fixed at one end to allow radial compliance as selected heating of the legs causes flexure. Below the legs is a semiconductor substrate having a flow orifice aligned with a valve face. Flexure of the legs displaces the valve face relative to the flow orifice, thereby controlling fluid flow through the orifice.

19 Claims, 4 Drawing Sheets

THERMALLY-ACTUATED MICROMINIATURE VALVE

TECHNICAL FIELD

The present invention relates generally to microminiature valves.

BACKGROUND ART

Many techniques used in the fabrication of electronic integrated circuit chips lend themselves readily to micromachining of mechanical devices such as valves. Microfabrication of mechanical devices is discussed by Angell et al. in "Silicon Micromechanical Devices," *Scientific American* (April 1983), pp. 44–55. Fabrication of a microminiature valve for use in gas chromatography is described. The analysis of gases in a silicon gas chromatograph is based on differences in the solubility of various gases in a liquid which lines the interior wall of a capillary through which the gases flow. Microminiature valves are used as gas flow regulators, as for example in setting the flow of a carrier gas through such a capillary. Some mechanical actuation means must be provided for such valves.

Solenoid actuation of a valve in a gas chromatography assembly is described in Terry et al. U.S. Pat. No. 4,474,889. However, John H. Jerman, a coinventor of the Terry et al. device, noted in a June, 1990 IEEE transaction that such actuation is not attractive because of the difficulties involved in providing sufficient actuation force ("Electrically-Activated, Micromachined Diaphragm Valves" by Jerman, *Technical Digest, IEEE Sensor and Actuator Workshop*, June 1990, pp. 65–69). Other difficulties associated with solenoid actuated valves are that they are expensive and that a substantial portion of such a valve cannot be batch-fabricated by using known microfabrication technology.

Other means for actuating a micromachined valve are known. O'Connor U.S. Pat. No. 4,581,624 teaches use of electrostatic force to deflect a flexible diaphragm until the diaphragm seals an outlet aperture valve seat. However, providing sufficient force for reliable actuation is a problem. Sittler et al. U.S. Pat. No. 4,869,282 teaches a micromachined valve which is actuated in part by gas pressure differentials at various ports of the valve. Such a valve is necessarily complex, and requires control gases to operate.

The above-identified paper by Jerman teaches use of a bi-metallic diaphragm consisting of a pair of materials, not necessarily metals, which are bonded together. The micromachined bi-metallic diaphragm has a lower surface of silicon and an upper surface of aluminum. As the temperature of the diaphragm is changed, stresses that are generated in the structure cause a deflection which moves the diaphragm and a downwardly-depending center boss relative to an outlet surrounded by a valve seat. In a normally-open embodiment, the center boss is moved toward the valve seat by the heat-induced deflection of the diaphragm. This deflection closes an otherwise open path to the outlet, thereby cutting off a flow of fluid to a system.

The bi-metallic structure taught by Jerman follows the teachings of the prior art. That is, the bimetallic structure is a solid circular diaphragm which is deflected to regulate fluid flow. The improvement of the structure is that the solenoid actuator of Terry et al. is replaced by a deposit of aluminum on a silicon diaphragm layer. Thus, the bi-metallic structure may be batch-processed in its entirety using known microfabrication technology. However, the valve is less than ideal. One problem involves the nonlinear deflection vs. force characteristics of the diaphragm. A microminiature valve may be required to open or close against a pressure of 200 pounds per square inch (psi). A diaphragm displacement of 40 microns may also be required. Such diaphragm displacement varies as the cube root of actuation force for large displacements, and this effect nonlinearity disproportionately increases in significance with an increase in deflection. In the deflected state, the valve is wasteful, since little deflection, and therefore little work, is performed by increases in force after a significant opening has already been achieved. Moreover, the bi-metallic diaphragm raises new considerations, such as thermal isolation of the diaphragm from the frame which supports the diaphragm to avoid excessive heat loss. It is important that the power supplied to a microminiature valve be efficiently utilized, but Jerman does not teach an efficient valve.

It is an object of the present invention to provide a microminiature valve which efficiently produces work throughout the entirety of a large range of displacement.

SUMMARY OF THE INVENTION

The above object has been met by a displaceable valve face, or "flap", which opens and closes a valve aperture, wherein the displaceable valve face is one face of a central body that is supported in one embodiment by multiple legs, arrayed like the legs of a spider around that central body. The legs are rigidly fixed at one end and are suspended at a second end in a manner to accommodate flexing.

The central body and legs combine to form a first deflectable member, designated the actuator member. The microminiature valve includes a second member, designated the orifice member, consisting of a rigid seat substrate having a central flow orifice surrounded by a raised valve seat. The actuator member is positioned atop the orifice member. The valve face on the bottom of the central body is aligned with the central flow orifice on the top of the orifice member. The microminiature valve may be normally-closed or normally-open, depending upon the orientation of the fixed and flexibly supported ends of the legs.

The legs have at least two layers. First and second layers of the legs are made of materials having substantially different coefficients of thermal expansion. As the legs are heated, the legs are caused to arch by differential expansions of the first and second layers, thereby causing a displacement of the valve face relative to the central flow orifice of the orifice member.

The flexible support of one end of the legs is accomplished by a torsion-bar suspension. This suspension accomplishes a hinge-like support of one end of each leg. Either the inner end proximal to the central body or the end distal from the central body may have the torsion-bar suspension. If the suspension is placed on the inner ends of the legs, the valve will close when actuated; if placed on the outer ends, it will open.

When placed on the outer ends, the suspension accomplishes the further purpose of minimizing loss from the hot legs to the ambient-temperature seat substrate by both decreasing the cross-section area and increasing the path length through which heat flow can occur.

When the valve is optimized for operation at higher pressures, such as several hundred PSI, the valve flap and legs may exceed in thickness the travel which the flap will undergo while opening. Under these circumstances, the flap member may optionally be made a larger portion of the diameter of the actuator member, and the legs reduced in length or eliminated entirely. This design variation is permissible since such a large flap does not, due to its thickness, flex sufficiently to enter the undesirable cube-law force region; i.e., that region in which the force required to deflect a diaphragm is no longer linearly related to the distance the diaphragm is deflected. In general, the force required to deflect a flat plate or diaphragm element includes both a term which increases linearly with displacement and a term which increases as the cube of displacement. For displacements less than approximately the thickness of the element, the linear term is dominant and the element is considered to act as a rigid plate; whereas for displacements much more than the thickness, the cube-term dominates and the element is considered to act as a thin, flexible diaphragm. In the cube-law region the force required builds up very rapidly; to double the deflection, eight times more force is required.

Thus a key element of the present design is avoidance of the cube-law disadvantage of the prior art. This goal is accomplished by minimizing the radius of the flap such that its dome-like deflection during operation does not substantially exceed its thickness, and is desirably much less than its thickness. The legs in the present invention comprise bending beams which are not subject to the cube-law effects that occur in diaphragms.

A final element of the invention is a rigid support of the unhinged ends of the legs. This may be accomplished by a circumferential ring of bi-morph structure. This ring is normally nominally as wide in a radial direction as each leg is wide. This function, for the normally-closed embodiment, is accomplished by the flap portion of the first deflectable member.

The factors to be considered in choosing materials for constructing the actuator member include coefficients of thermal expansion, melting points, strengths, and ease of use in integrated circuit fabrication processes. Preferably, the coefficient of thermal expansion of the second layer is greater than that of the first layer by at least 5 PPM/C. Typically, the first layer, closest to the seat substrate member, is silicon. The second layer is a material chosen to generally have a high strength, a high coefficient of thermal expansion, and a reasonably high melting point. Strength and melting point are factors, since plastic deformation of the legs limits the range of temperatures over which the valve can operate. Nickel rates well against these parameters, and is amenable to fabrication by both plating and deposition.

In the normally-closed embodiment, the ends of the legs distal from the central body are connected by the torsion-bar suspension, and the proximal ends are rigidly connected to the central body. The spider legs are typically radially extending members, but this is not critical. The suspension is implemented by typically two rings of circumferential slots. Metal film resistors on the legs or on the central body act as heaters for introduction of thermal energy to arch the spider legs. An electrical current in the resistors heats the actuator member. Typically the actuator member is composed of two major layers and is referred to as a "bimorph" structure.

Advantages of the present invention include the efficiency-enhancing linearity accomplished as described above by avoiding the cube-law region of dome deflection. Another advantage is the inclusion of the suspension, which improves thermal isolation, and provides a hinge-like attachment of one end of the membrane structure. A third advantage is the presence of openings between the legs in near proximity to the orifice region to minimize the occurrence of unswept flow volumes.

By embodying an improved suspension with improved linearity, the microminiature valve operates more reliably and with much higher performance in terms of flow and pressures, than does the prior art.

BEST MODE FOR CARRYING OUT THE INVENTION

Figure 1:
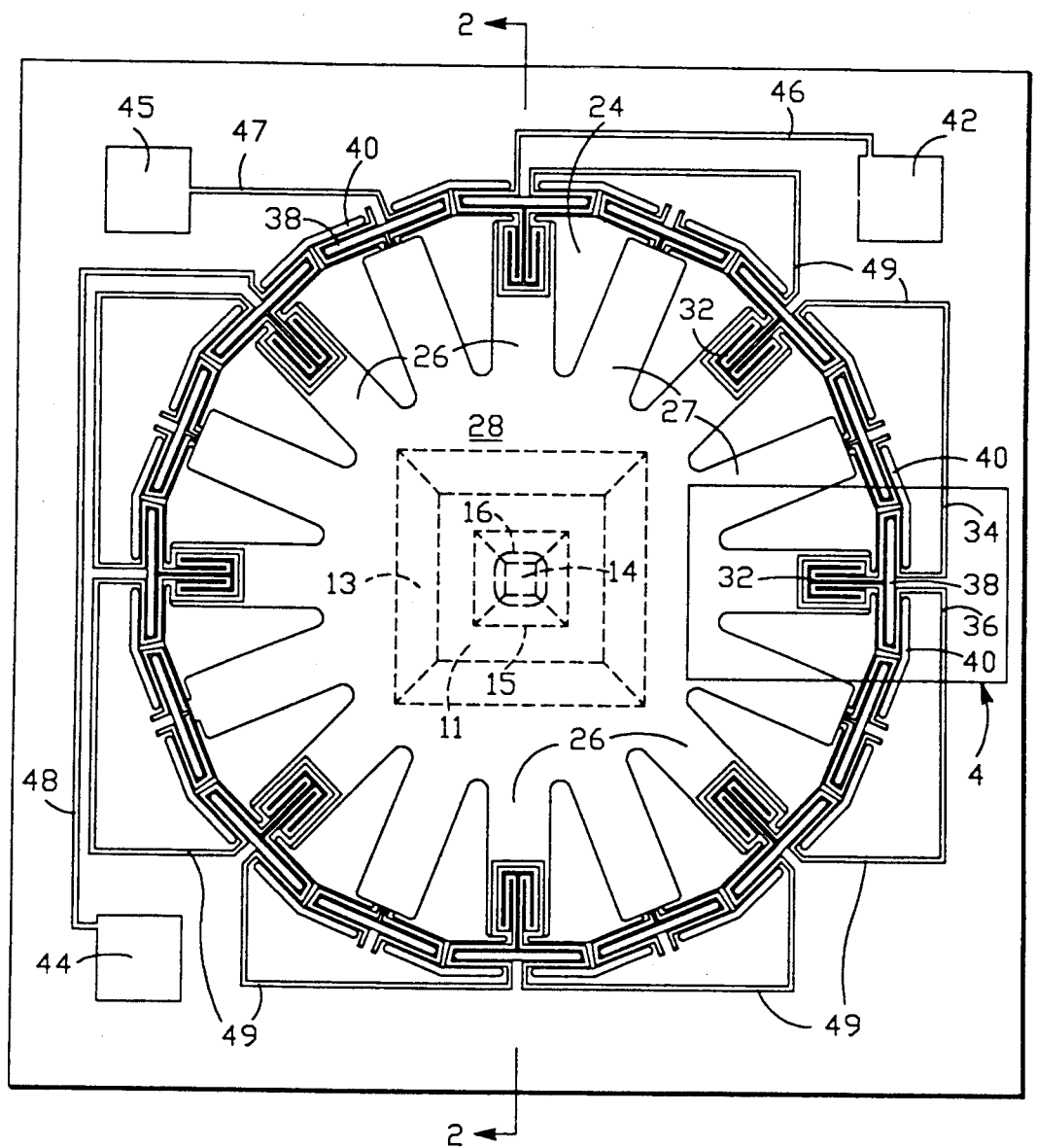
FIG. 1 is a top view of a first embodiment of a microminiature valve in accord with the present invention.
Figure 2:
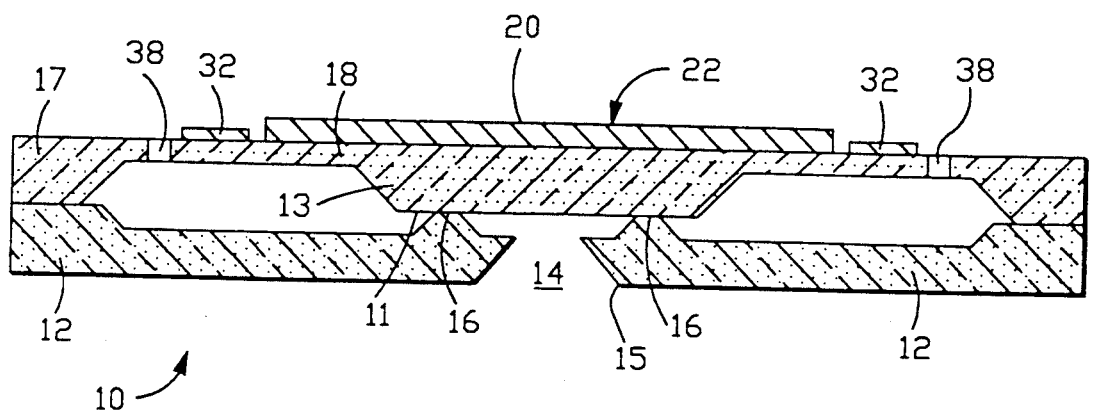
FIG. 2 is a side sectional view of the valve of FIG. 1, taken along lines 2—2 and shown in a closed position.

With reference to FIGS. 1 and 2, a microminiature valve 10 is shown as including a seat substrate 12 which acts as a base. A central flow orifice 14 is anisotropically etched through the seat substrate 12. The etching provides the truncated pyramidal shape having a lower periphery 15 illustrated in the drawings. The upper surface of the substrate 12 is also etched, leaving a valve seat 16 that surrounds the flow orifice 14. The flow orifice and the valve seat are shown in phantom in FIG. 1 through upper layers of the microminiature valve.

The seat substrate 12 is preferably a silicon chip which has been fabricated from a wafer using batch processing steps well known in the art of micromachining. The microminiature valve 10 is 7 mm by 7 mm, but this is not critical. At its periphery, the seat substrate 12 is 400 microns thick.

As shown in FIG. 2, supported atop the seat substrate 12 is a second substrate that includes a fixed periphery 17 and a central flexible member 22. The length and the width of the second substrate match the dimensions of the seat substrate 12. As will be explained more fully below, the fixed periphery 17, a lower layer 18 of the flexible member, and a downwardly-depending boss 13 are formed from a single silicon substrate. The thickness of the silicon layer 18 in a preferred embodiment is 30 microns, but since the thickness is a factor in determining the amount of maximum opening of the microminiature valve 10, the ideal thickness of the silicon layer will vary according to application.

Figure 3:
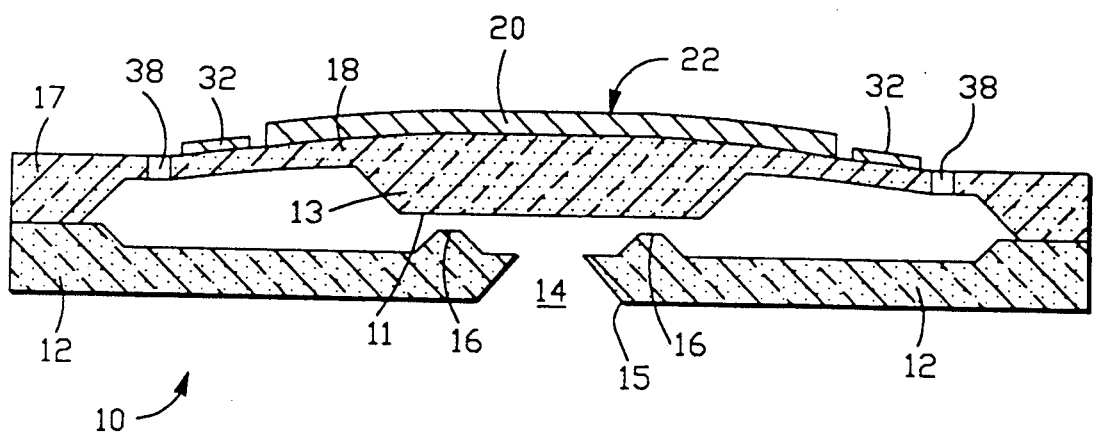
FIG. 3 is a side sectional view of the valve of FIG. 2 in an open position.

A layer of nickel 20 is deposited and patterned on the silicon layer 18, using the techniques of evaporation, photolithography, and electroplating. In practice, the thickness of the nickel layer is approximately 30 microns and approximately equal to the thickness of the silicon layer. FIG. 3 shows the composite silicon and nickel structure in an open position.

Figure 4:
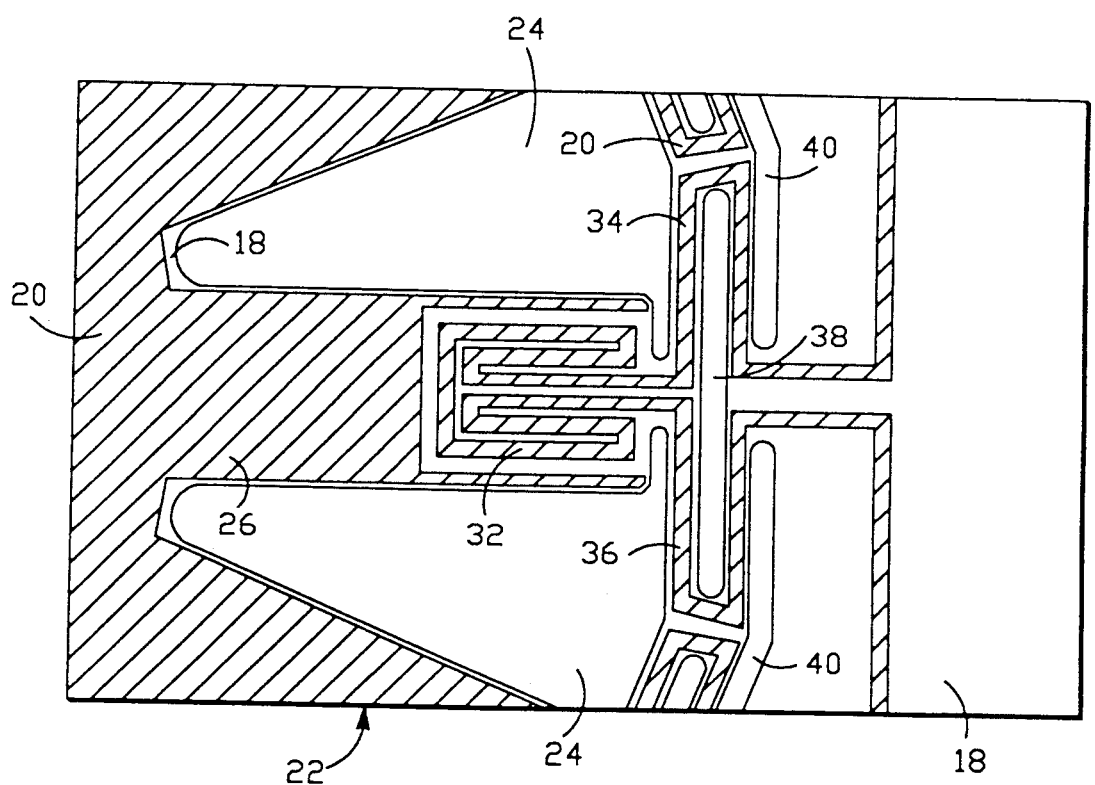
FIG. 4 is a top view of the segment of the valve of FIG. 1 shown in rectangle 4.

FIGS. 1 and 4 best illustrate the structure of the flexible member 22 for the microminiature device. Nickel covers only a portion of the flexible member. Both the silicon and nickel layers have roughly triangular openings 24 that define an array of spider legs 26 and 27 in the flexible member 22. In operation, upon opening of the valve, gas will flow through the openings 24 and through the flow orifice 14 described above.

Each leg 26 and 27 is rigidly connected at a radially inward end to a central body 28. Each leg 26 includes a serpentine pattern of nickel which acts as a heating element 32. Conduction of a current through the heating elements generates localized heating which then conducts through the silicon and nickel layers 18 and 20 that make up the legs 26. The heated legs 26 are spaced apart by legs 27 not having heating elements 32. Each of the eight heating elements has an impedance of approximately 5 ohms. Either an analog signal or a more efficient digital pulse-width modulated signal may be used to drive the valve.

The heating elements 32 have a thickness of 1 micron to achieve the 5 ohm impedance. Electrical paths to and from each heating element are serpentine metal depositions 34 and 36 on the silicon layer 18, arranged such that the heating elements are series-connected. For example, deposition path 34 may be at ground potential, while deposition path 36 continues the series connection to the next element. Current through the metal deposition paths may cause the temperature of the legs to rise approximately 100° C. over ambient temperature, and the valve would thereby fully open.

Each leg 26 and 27 is associated with a plurality of circumferential slots 38 and 40 formed through both the silicon layer 18 and the nickel layer 20. The slots serve three roles. Firstly, the slots provide a large degree of thermal isolation of the legs from the silicon layer radially beyond the legs. Thus, less power is needed to achieve a desired deflection of the legs. Secondly, the circumferential slots 38 and 40 provide rotational flexibility at the boundaries of the legs. The flexibility accommodates the movement experienced at these boundaries as the legs expand and arch during heating cycles and contract upon relaxation. Thirdly, the slots provide lateral flexibility in addition to rotational flexibility, so that the tendency of the legs 26 to pull inwardly as they arch can be accommodated.

As illustrated in FIG. 1, the upper surface of the valve includes a pair of conductive pads 42 and 44. A drive circuit, not shown, is electrically connected to the pads to channel a current to the heating elements 32, via traces 46, 48 and 49. An additional pad 45 and trace 47 are shown. During fabrication, the pad 45 and trace 47 are connected to a metal grid for maintaining contact of the substrate to the metal grid during electroplating of the nickel layer.

In a preferred embodiment, fabrication proceeds as described below. In a first wafer of silicon, designated the orifice wafer, well-established batch-fabrication, silicon micromachining techniques are used to fabricate raised valve seats 16 surrounding central flow orifices 16. Following these fabrication steps the orifice wafer is separated by sawing the wafer into individual orifice chips, and each orifice chip is cleaned.

A second wafer of silicon, designated the actuator wafer, is treated as follows. First, a layer of silicon dioxide is grown, and then a layer of silicon nitride is deposited, on both major surfaces of this second wafer. These layers are photolithographically patterned on the top surface of the wafer to form holes in areas which will later be etched completely through the silicon in the regions 24 between the spider legs 26 and 27. The silicon dioxide and silicon nitride layers are patterned on the bottom surface of the wafer to define regions on the bottom side of the wafer which will become the boss 13 on the bottom of the central body 28 of each flexible member 22 and the thickness of the legs 26 and 27 surrounding the central body. Next, a layer 20 of nickel is deposited on the top surface using evaporation or sputtering, and this nickel is patterned to leave both thin-film resistor regions 32 and other regions which will later be electroplated with thick nickel. Then, a layer of photoresist is deposited and is photolithographically patterned and etched to define holes through the photoresist in the regions which will later be etched completely through the silicon in the regions between the spider legs, and to define holes in the photoresist to the nickel layer in areas which will be plated up. Next, such electroplating is carried out to form thick nickel regions. As noted above, a continuous metal grid is used in the electroplating process. The pad 45 is added to the structure for the purpose of maintaining contact to the metal grid. The grid is later broken upon sawing of the wafer into individual chips. The photoresist is further used to mask against plasma etching, which is employed to etch pits into the silicon to a depth slightly greater than the final thickness of the spider legs.

The top surface of the actuator wafer is then protected by being adhered with wax onto a glass plate, and the back surface of the wafer is etched in aqueous potassium hydroxide, forming the boss 13 on the bottom side of the actuator wafer, and also forming the spider legs 26 and 27 as the etching from the bottom side reaches the pits which had previously been etched from the topside. The actuator is then removed from the glass plate, and is separated into individual actuator chips by sawing, and the actuator chips are cleaned.

Finally, an individual actuator chip is bonded to an individual orifice chip by placing the surfaces of the two chips together and forming a bead of adhesive such as epoxy adhesive at the exposed edges of the two chips. Following curing of the adhesive, the resulting completed valve structure can be packaged.

Other materials may be used in place of the nickel. The upper layer 20 of the legs 26 should have a coefficient of thermal expansion substantially different than that of the silicon layer. Moreover, the upper layer should have a high melting point so that plastic deformation does not occur during normal operation. Nickel is the preferred metal, with copper being a good substitute. Aluminum, as used in prior art, is not the preferred choice for this structure for two reasons. Firstly, aluminum cannot be electroplated from aqueous solutions and so cannot be fabricated into thick, patterned layers on bimorphic structures as can materials such as nickel or copper. The deposition of thick aluminum layers by known processes such as thermal evaporation or sputtering would be wasteful and expensive, and the patterning of such layers by photolithographic techniques would be difficult and wasteful of active area in the resulting structure. Secondly, aluminum has a low yield strength in comparison to nickel or copper, and so is unsuitable both for large actuation forces and for stable device characteristics over time. Likewise, use of silicon for the lower layer 18 of the legs is not critical. However, silicon allows use of well-known fabrication processes. As an alternative to the film resistors 32, diffused resistors or active diffused devices such as transistors may be employed.

In operation, FIG. 2 shows the microminiature valve 10 in a closed condition in which the boss 13 abuts the valve seat 16 to prevent flow into the fluid flow orifice 14. In this embodiment, the entire operating region of the silicon layer 18 is coated with nickel 20. That is, the electroplated nickel extends over the central region of the silicon layer, rather than being limited to the radially extending legs 26. As thermal energy is conducted out of the heating elements 32 and into the legs, the difference in coefficients of thermal expansion of the silicon layer and the nickel layer causes the legs to arch downwardly, thus lifting the boss 13 away from the valve seat 16 and opening the valve.

In FIGS. 1-4, a rigid suspension is at the radially inner ends of the spider legs 26 and a flexible suspension is provided by the circumferential slots 38 and 40 at the radially outer ends. Thermal expansion generates a force at the suspensions. The circumferential slots allow the spider legs to arch, thereby causing displacement of the valve face 28 relative to the flow orifice 14. With the flexible suspension at the radially outer ends, the boss 13 will move from the normally closed position of FIG. 2 to the open position of FIG. 3.

Figure 5:
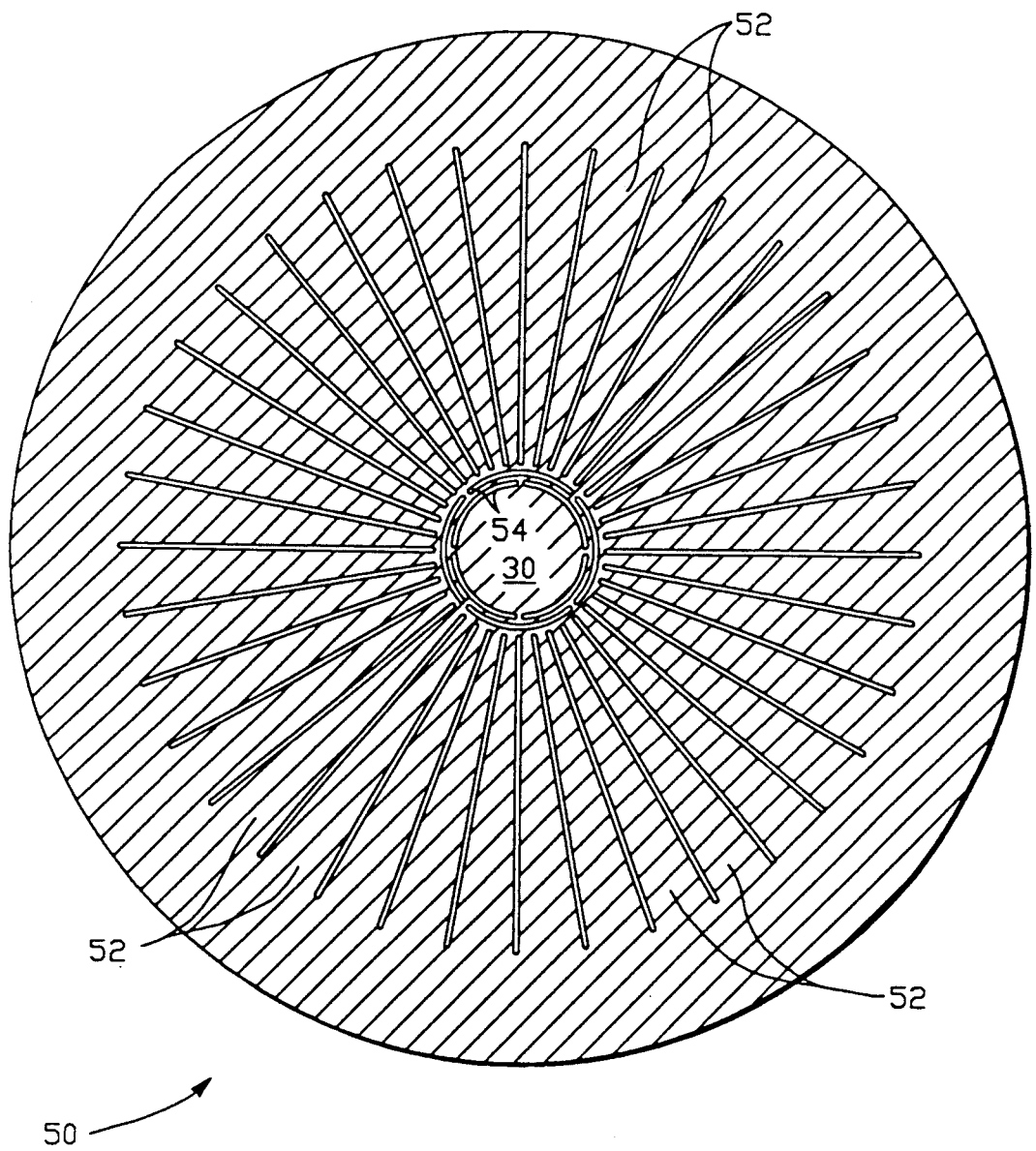
FIG. 5 is a top view of a second embodiment of the present invention.

In comparison, in the embodiment of FIG. 5 circumferential slots 54 at inner ends of legs 52 of a microminiature valve 50 allow downward arching of the legs 52. Thus, the valve face 30 of the second embodiment is displaced downwardly to seal a flow orifice, not shown, upon heating of the legs 52. The microminiature valve 50 is therefore a normally-open valve.

Returning to the embodiment of FIGS. 1-4, the circumferential slots 38 and 40 thereby provide a torsion bar hinge that allows radial compliance, rotation, and thermal isolation. In operation, heating the legs 26 and 27 causes the flexible member 22 to displace upwardly and open the flow orifice 14. The mechanism whereby this happens is that when the legs are heated they become arched. Since they are attached rigidly at their innermost ends, their outermost extremities curve downwardly, exerting a force against the suspension to lift the boss 13.

The arching has a secondary tendency of pulling the legs inwardly. Restraining this tendency would inhibit lifting action. Removing material to form the slots 38 and 40 within the silicon and nickel layers 18 and 20 allows radial movement of the legs 26 and 27.

By applying an appropriate control signal to the valve, it may be caused to open a controllable amount of between 0 and 30 microns.

One intended application of the microminiature valve 10 is gas chromatography. The valve controls gas flow from a tank into an injection reservoir of a gas chromatograph. A flow sensor measures flow and provides a feedback to electrically control the valve to adjust gas flow to the amount desired. The valve is able to control 200 psi at a flow up to 400 sccm. An actuation time of several hundred milliseconds is typical.

Closing of the microminiature valve 10 occurs upon conductive cooling of the legs 26 and 27, via heat flow out through the suspension and into the seat substrate 12. The speed of the valve is largely determined by the thermal mass of the flexible member 22 and the thermal resistance of the suspension.

The second embodiment of FIG. 5 is a normally-open microminiature valve 50 that operates in the same manner as the first embodiment. The microminiature valve includes thirty-six legs 52. A layer of nickel covers a circular layer of silicon. As the legs 52 are heated, the legs bend to close a valve seat, not shown, directly below the valve face 30. Displacement of the valve face is downward because the flexural suspension provided by the circumferential slots 54 is at the inner ends of the legs 52. Again, the slots 54 provide flexural and radial compliance as the legs 52 are heated.

Higher operating pressures may be obtained in both the first and second embodiments by increasing the thickness of the first flexible member 22. The number of legs on the microminiature valve is not critical. The shape of the legs is important, but not critical. A spiral of legs is a possible alternative to the radially extending legs. It may be desirable in some applications to exclude the downwardly-depending boss 13.

What is claimed:

1. A microminiature valve for controlling the flow of a fluid comprising,
    a seat substrate having a flow orifice defined therethrough,
    a flexural member coupled to said seat substrate to selectively block said flow orifice, said flexural member having a central flap in alignment with said flow orifice and having a plurality of spaced, layered regions extending from said central flap to a peripheral region, first and second layers of said layered regions having substantially different coefficients of thermal expansion, and
    heating means thermally coupled to said layered regions for selectively flexing said layered regions by differential expansions of said first and second layers, wherein said flexing causes displacement of said central flap relative to said flow orifice.

2. The valve of claim 1 further comprising suspension means for supporting said layered regions to one of said central flap and said peripheral region, said suspension means having slots aligned to accommodate rotational motion and thermal expansion of said layered regions, second ends of said layered regions opposite to said suspension means being rigidly fixed.

3. A valve as in claim 2 wherein said second ends attach to a bimorph ring of width greater than half the width of said layered regions.

4. The valve of claim 1 wherein said layered regions are bimorphic, radially extending spider legs.

5. The valve of claim 4 wherein said spider legs are spaced apart by open areas.

6. The valve of claim 1 wherein said first layer is silicon and said second layer is nickel.

7. The valve of claim 1 wherein said central flap of said flexural member is a layered valve face having first and second layers having substantially different coefficients of thermal expansion.

8. The valve of claim 1 wherein said heating means includes electrically conductive metal film resistors operatively coupled to each layered region.

9. The valve of claim 2 wherein said slots are circumferential slots and are at ends of said layered regions opposite to said central flap.

10. A micromachined valve comprising,
    a semiconductor base having a fluid flow path therein, said fluid flow path having a terminus at a valve seat,
    a valve face aligned with said valve seat at said terminus,
    a plurality of spider legs having first ends attached to said valve face, said spider legs having first and second layers of distinct materials having substantially different coefficients of thermal expansion, and
    support means attached to said second ends of said spider legs for aligning said valve face with said valve seat.

11. The valve of claim 10 further comprising heating means for selectively increasing the temperature of said spider legs.

12. The valve of claim 10 wherein the coefficient of thermal expansion of said second layer exceeds the coefficient of thermal expansion of said first layer by at least 5 PPM/°C.

13. The valve of claim 10 wherein all of said valve face, said first layer of said spider legs and said support means include a single unitary semiconductor substrate.

14. The valve of claim 13 wherein said support means includes circumferential slots in said semiconductor substrate at one of said first and second ends of said spider legs.

15. The valve of claim 13 wherein said second layer is a nickel layer.

16. The valve of claim 14 wherein said spider legs extend radially from said valve face and wherein said circumferential slots are at said second ends, said valve being a normally-closed valve.

17. The valve of claim 14 wherein said spider legs extend radially from said valve face and wherein said circumferential slots are at said first ends, said valve being a normally-open valve.

18. A microminiature valve for controlling flow of a fluid comprising, a base having a flow orifice defined therethrough, a flexural member coupled to said base for regulating flow through said flow orifice, said flexural member having a center region aligned with said flow orifice, said flexural member having a thermally-actuated region and a set of generally circumferential slots on an outer radial side of said thermally-actuated region, said thermally-actuated region having first and second layers having substantially different coefficients of thermal expansion, said circumferential slots promoting thermal isolation and movement of the thermally-actuated region relative to said outer radial side, and heating means thermally coupled to said flexural member for selectively displacing said center region relative to said flow orifice by differential expansions of said first and second layers.

19. The valve of claim 18 wherein said flexural member has an array of radially extending legs.

* * * * *